United States Patent
Mitsuda et al.

(10) Patent No.: US 6,344,569 B1
(45) Date of Patent: Feb. 5, 2002

(54) PROCESS FOR PRODUCING 6-CYANOMETHYL-1,3-DIOXANE-4-ACETIC ACID DERIVATIVES

(75) Inventors: Masaru Mitsuda, Akashi; Makoto Miyazaki, Amagasaki; Kenji Inoue, Kakogawa, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/674,178
(22) PCT Filed: Apr. 28, 1999
(86) PCT No.: PCT/JP99/02272
  § 371 Date: Jan. 2, 2001
  § 102(e) Date: Jan. 2, 2001
(87) PCT Pub. No.: WO99/57109
  PCT Pub. Date: Nov. 11, 1999

(30) Foreign Application Priority Data

Apr. 30, 1998 (JP) .......................................... 10-121135

(51) Int. Cl.⁷ ....................... C07D 319/06; C07C 253/14
(52) U.S. Cl. ........................................ 549/375; 558/342
(58) Field of Search ........................... 549/375; 558/342

(56) References Cited

U.S. PATENT DOCUMENTS 5,103,024 A * 4/1992 Millar et al. ................. 549/373
5,278,313 A * 1/1994 Thottathil et al. ........... 548/252

* cited by examiner

*Primary Examiner*—Floyd D. Higel
*Assistant Examiner*—Andrea M D'Souza
(74) *Attorney, Agent, or Firm*—Connolly Bove Lodge & Hutz

(57) ABSTRACT

The present invention provides a process which can produce an important intermediate for the production of the HMG coenzyme A reductase inhibitor atrovastatin, 6-cyanomethyl-1,3-dioxane-4-acetic acid derivatives, with ease industrially and in good yields, wherein a 3,5-dihydroxy-6-halohexanoic acid derivative is used as the starting material, and which comprises cyanation by reaction with a cyanating agent for substitution of a cyano group for the halogen atom and an acetal formation reaction of the diol moiety with an acetal forming reagent in the presence of an acid catalyst.

12 Claims, No Drawings

PROCESS FOR PRODUCING 6-CYANOMETHYL-1,3-DIOXANE-4-ACETIC ACID DERIVATIVES

This application is a 371 of PCT/JP99/0227 Apr. 28, 1999.

TECHNICAL FIELD

The present invention relates to a process for producing 6-cyanomethyl-1,3-dioxane-4-acetic acid derivatives by which process an intermediate of medicinal compounds, in particular 1,1-dimethylethyl (4R,6R)-6-cyanomethyl-2,2-dimethyl-1,3-dioxane-4-acetate (formula (9)), (9)

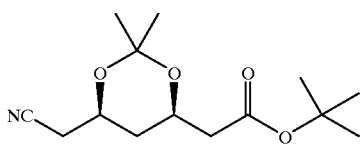

which is an important intermediate for the production of the HMG coenzyme A reductase inhibitor atrovastatin (described in International Patent Application 93/07115 pamphlet), and the like, can be produced.

BACKGROUND ART

In the International Patent Application 89/07598 pamphlet, there are disclosed a process starting with isoascorbic acid and a process starting with an optically active epoxide for the production of 1,1-dimethylethyl (4R,6R)-6-cyanomethyl-2,2-dimethyl-1,3-dioxane-4-acetate. For the production thereof from raw materials readily available on the market, however, either process requires an excessively large number of steps and is complicated.

A process is disclosed in the specification of U.S. Pat. No. 5,103,024 which starts with (4R-cis)-1,1-dimethylethyl 6-hydroxymethyl-2,2-dimethyl-1,3-dioxane-4-acetate and derives the desired substance therefrom by two steps, namely conversion to an arylsulfonate and cyanation. However, the starting material disclosed therein is expensive and a multistep synthetic process is required for the preparation of the starting material itself from commercially available materials.

In the specification of U.S. Pat. No. 5,155,251, a process for the production of the desired product is disclosed which comprises cyanating an (S)-4-chloro-3-hydroxybutyric acid ester, reacting with an enolate anion derived from tert-butyl acetate to provide (5R)-1,1-dimethylethyl 6-cyano-5-hydroxy-3-oxohexanoate, and stereoselectively reducing the ketone carbonyl group of the same with a hydride, followed by conversion of the resulting 1,3-diol to the corresponding acetonide.

In the International Patent Application 97/00968 pamphlet, there is disclosed a process for producing the desired product which comprises stereoselectively reducing (5R)-1,1-dimethylethyl 6-cyano-5-hydroxy-3-oxohexanoate with a microorganism, followed by conversion of the resulting 1,3-diol to the corresponding acetonide.

While the compound (5R)-1,1-dimethylethyl 6-cyano-5-hydroxy-3-oxohexanoate, which is commonly used in the processes described in the specification of U.S. Pat. No. 5,155,251 and the Laid-open International Patent Application 97/00968 pamphlet, can be prepared by the process described in the specification of U.S. Pat. No. 5,155,251, investigations by the present inventors revealed that, in the cyanation reaction of the (S)-4-chloro-3-hydroxybutyric acid ester in that process, an unfavorable side reaction, namely a side reaction resulting from epoxide formation under the reaction conditions (J. Org. Chem., 32 (1967), p. 3888) proceeds, resulting in decreases in reaction yield and product purity.

Accordingly, it is an object of the present invention to provide a process for producing a 6-cyanomethyl-1,3-dioxane-4-acetic acid derivative of the general formula (3), which is an important intermediate of medicinal compounds.

(3)

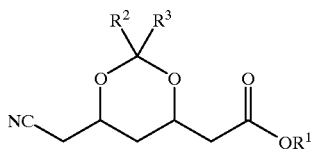

wherein $R^1$, $R^2$ and $R^3$ each independently represents a hydrogen atom, an alkyl group containing 1 to 12 carbon atoms, an aryl group containing 6 to 10 carbon atoms or an aralkyl group containing 7 to 12 carbon atoms, and an optically active isomer thereof from a raw material readily available on the market, at low cost and in high yields.

SUMMARY OF THE INVENTION

The present inventors made intensive investigations in an attempt to solve the above problems and, as a result, succeeded in developing a process which uses, as the starting material, a 3,5-dihydroxy-6-halohexanoic acid derivative of the general formula (1):

(1)

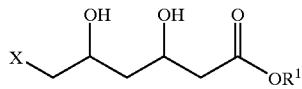

wherein $R^1$ represents a hydrogen atom, an alkyl group containing 1 to 12 carbon atoms, an aryl group containing 6 to 10 carbon atoms or an aralkyl group containing 7 to 12 carbon atoms, and X represents a halogen atom, which can be readily prepared from a 4-chloro-3-hydroxybutyric acid ester readily available on the market in good yields by a per se known two step process, for instance, and by which 6-cyanomethyl-1,3-dioxane-4-acetic acid derivatives of the general formula (3):

(3)

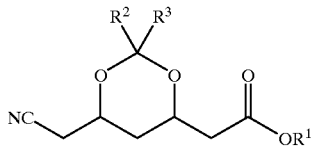

wherein
  $R^1$ is as defined above, and $R^2$ and $R^3$ each independently represents a hydrogen atom, an alkyl group containing 1 to 12 carbon atoms, an aryl group containing 6 to 10 carbon atoms or an aralkyl group containing 7 to 12 carbon atoms,
  can efficiently be produced by a two step process.

The invention thus provides a process for producing a 6-cyanomethyl-1,3-dioxane-4-acetic acid derivative of the above general formula (3)

which comprises cyanation of a 3,5-dihydroxy-6-halohexanoic acid derivative of the above general formula (1) by reaction with a cyanating agent for substitution of a cyano group for the halogen atom and an acetal formation reaction of the diol moiety with an acetal forming reagent in the presence of an acid catalyst.

The above process is realized by reacting the 3,5-dihydroxy-6-halohexanoic acid derivative of the above general formula (1) with a cyanating agent to provide a 6-cyano-3,5-dihydroxyhexanoic acid derivative of the general formula (2):

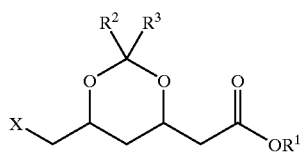

(2)

wherein

R$^1$ is as defined above, followed by an acetal formation reaction of the same with an acetal forming reagent in the presence of an acid catalyst, or by subjecting the 3,5-dihydroxy-6-halohexanoic acid derivative of the above general formula (1) to an acetal formation reaction with an acetal forming reagent in the presence of an acid catalyst to provide a 6-halomethyl-1,3-dioxane-4-acetic acid derivative of the general formula (7):

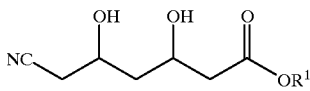

(7)

wherein R$^1$, R$^2$, R$^3$ and X are as defined above, followed by cyanating it with a cyanating agent.

In particular, the present inventors newly found that the substitution reaction of X which proceeds upon reacting a 3,5-dihydroxy-6-halohexanoic acid derivative of the above general formula (1) with a cyanating agent proceeds very effectively owing to the neighboring group effect by the hydroxyl group adjacent to X and, as a result, the corresponding 6-cyano-3,5-dihydroxyhexanoic acid derivative of the above general formula (2) can be produced with great efficiency.

It was further found by the present inventors that when an optically active 3,5-dihydroxy-6-halohexanoic acid derivative is used as the starting material, the corresponding optically active 6-cyano-3,5-dihydroxyhexanoic acid derivative and optically active 6-cyanomethyl-1,3-dioxane-4-acetic acid derivative can be produced, with the configuration of each center of asymmetry being retained.

In the following, the present invention is explained in detail.

DETAILED DISCLOSURE OF THE INVENTION

Two routes were found by the present inventors for the production of a 6-cyanomethyl-1,3-dioxane-4-acetic acid derivative (3) from the corresponding 3,5-dihydroxy-6-halohexanoic acid derivative (1), as shown by the scheme 1 given below.

Scheme 1

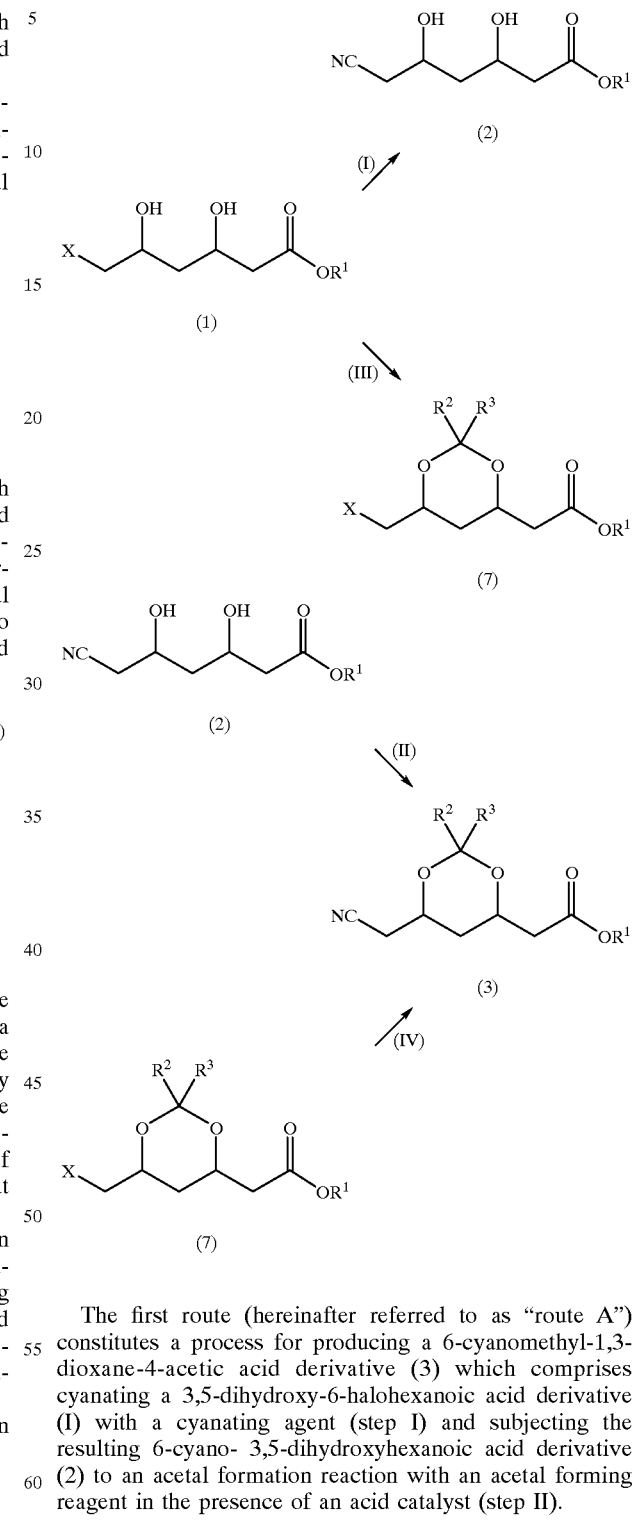

The first route (hereinafter referred to as "route A") constitutes a process for producing a 6-cyanomethyl-1,3-dioxane-4-acetic acid derivative (3) which comprises cyanating a 3,5-dihydroxy-6-halohexanoic acid derivative (I) with a cyanating agent (step I) and subjecting the resulting 6-cyano- 3,5-dihydroxyhexanoic acid derivative (2) to an acetal formation reaction with an acetal forming reagent in the presence of an acid catalyst (step II).

The second route (hereinafter referred to as "route B") constitutes a process for producing a 6-cyanomethyl-1,3-dioxane-4-acetic acid derivative (3) which comprises subjecting a 3,5-dihydroxy-6-halohenxanoic acid derivative (1) to an acetal formation reaction with an acetal forming reagent in the presence of an acid catalyst (step III) and cyanating the resulting 6-halomethyl-1,3-dioxane-4-acetic acid derivative (7) with a cyanating agent (step IV).

Referring to the common starting material for route A and route B, namely the 3,5-dihydroxy-6-halohexanoic acid derivative of the general formula (1):

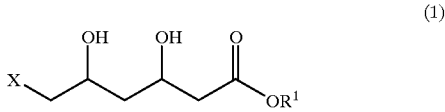
(1)

R¹ is a hydrogen atom, an alkyl group containing 1 to 12 carbon atoms, an aryl group containing 6 to 10 carbon atoms or an aralkyl group containing 7 to 12 carbon atoms.

As the above alkyl group containing 1 to 12 carbon atoms, aryl group containing 6 to 10 carbon atoms and aralkyl group containing 7 to 12 carbon atoms, there may be mentioned, for example, methyl, ethyl, 1,1-dimethylethyl, hexyl, dodecanyl, phenyl, tolyl, naphthyl, benzyl, p-methoxybenzyl, naphthylethyl and the like. Preferred among them is 1,1-dimethylethyl.

X is a halogen atom, preferably a chlorine, bromine or iodine atom, more preferably a chlorine atom.

For the 3,5-dihydroxy-6-halohexanoic acid derivative (1), which is a chiral compound having two asymmetric carbon atoms, there are four optical isomers, namely (3S, 5S), (3S, 5R), (3R, 5S) and (3R, 5R) isomers. In the present invention, all these optically active isomers can be used. It is also possible to use a 3,5-dihydroxy-6-halohexanoic acid derivative (1) which is a mixture composed of a plurality of such isomers. Preferred is the optically active (3R, 5S) isomer of the following general formula (4):

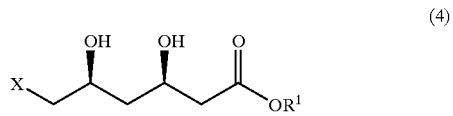
(4)

Accordingly, the most preferred 3,5-dihydroxy-6-halohexanoic acid derivative (1) is 1,1-dimethylethyl (3R, 5S)-6-chloro-3,5-dihydroxyhexanoate.

The 3,5-dihydroxy-6-halohexanoic acid derivative (1) can be prepared from a commercially available 4-chloro-3-hydroxybutyric acid ester with good yields in two steps by a per se known process, for instance. Thus, 1,1-dimethylethyl (3R, 5S)-6-chloro-3,5-dihydroxyhexanoate can be prepared from (S)-4-chloro-3-hydroxybutyric acid ester (e.g. the specification of U.S. Pat. No. 1,723,728), which can be produced on a high production scale, for example, by the process described in the specification of U.S. Pat. No. 5,278,313, according to the following scheme 2:

Scheme 2

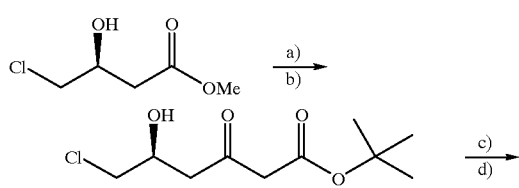

a) CH₃CO₂t-Bu/LHMDS/THF, b) AcOH,

-continued

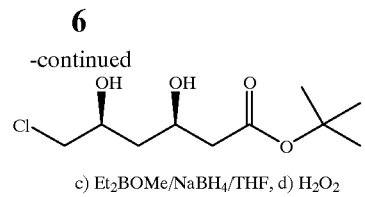

c) Et₂BOMe/NaBH₄/THF, d) H₂O₂

In step (I) of route A according to the present invention, a cyanide can be used as the cyanating agent. The cyanide includes, among others, sodium cyanide, potassium cyanide, calcium cyanide, silver cyanide, tetraethylammonium cyanide, tetrabutylammonium cyanide and the like. Sodium cyanide or potassium cyanide is preferred.

In step (I) of route A according to the present invention, the cyanating agent is used preferably in an amount of 1 to 5 molar equivalents, more preferably 1 to 2 molar equivalents, relative to the 3,5-dihydroxy-6-halohexanoic acid derivative (1).

As the solvent which can be used in step (I) of route A according to the present invention, there may be mentioned, for example, water and an organic solvent. The organic solvent includes, among others, alcohol type solvents such as methanol, ethanol, butanol, isopropyl alcohol, ethylene glycol and methoxyethanol; hydrocarbon type solvents such as benzene, toluene and cyclohexane; ether type solvents such as diethyl ether, tetrahydrofuran, 1,4-dioxane, methyl t-butyl ether and dimethoxyethane; ester type solvents such as ethyl acetate and butyl acetate; ketone type solvents such as acetone and methyl ethyl ketone; halogenated solvents such as methylene chloride, chloroform and 1,1,1-trichloroethane; nitrogen-containing solvents such as dimethylformamide, acetamide, formamide and acetonitrile; aprotic polar solvents such as dimethyl sulfoxide, N-methylpyrrolidone and hexamethylphosphoric triamide; and so forth. The above solvents may be used singly or two or more of them may be used in combination. Among the above-mentioned solvents, water, dimethylformamide, acetamide, formamide, acetonitrile, dimethyl sulfoxide, N-methylpyrrolidone and the like are preferred.

Instep (I) of route A according to the present invention, the reaction temperature is within the range of 0° C. to 150° C., preferably 20° C. to 100° C.

The reaction time in step (I) of route A according to the present invention may vary depending on the reaction conditions but generally is several minutes to 10 hours.

For recovering the product from the reaction mixture, a conventional procedure for posttreatment may be carried out. Thus, for example, water is added to the reaction mixture after completion of the reaction, and an extraction procedure is carried out using a conventional extraction solvent such as ethyl acetate, diethyl ether, methylene chloride, toluene, hexane or the like. The reaction solvent and extraction solvent are distilled off from the thus-obtained extract by a procedure such as heating under reduced pressure, whereupon the desired product is obtained. Such an extraction procedure may be carried out after distilling off the reaction solvent by a procedure such as heating under reduced pressure immediately following completion of the reaction. While the thus-obtained product is nearly pure, the purity may further be increased by purification using conventional means such as purification by crystallization, fractional distillation, column chromatography, etc.

The 6-cyano-3,5-dihydroxyhexanoic acid derivative of the general formula (2):

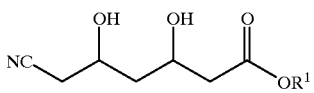

(2)

obtained in step (I) of route A according to the invention retains the configuration of each of the two asymmetric carbon atoms of the 3,5-dihydroxy-6-halohexanoic acid derivative (1) used and, thus, the (3S, 5S)-, (3S, 5R)-, (3R, 5S)- and (3R, 5R)-3,5-dihydroxy-6-halohexanoic acid derivatives give the corresponding (3S, 5R)-, (3S, 5S)-, (3R, 5R)- and (3R, 5S)-6-cyano-3,5-dihydroxyhexanoic acid derivatives, respectively. The (3R, 5R) isomer of the following general formula (5):

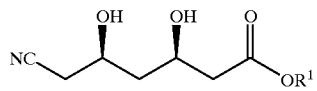

(5)

is preferred.

Therefore, the most preferred 6-cyano-3,5-dihydroxyhexanoic acid derivative (2), namely 1,1-dimethylethyl (3R, 5R)-6-cyano-3,5-dihydroxyhexanoate, can be produced from the most preferred 3,5-dihydroxy-6-halohexanoic acid derivative (1), namely 1,1-dimethylethyl (3R, 5S)-6-chloro-3,5-dihydroxyhexanoate.

In step (II) of route A according to the invention, the acetal forming reagent is not particularly restricted but includes a ketone, an aldehyde, an alkoxyalkane, an alkoxyalkene and so on. As specific examples of the above ketone, aldehyde, alkoxyalkane, alkoxyalkene, etc., there may be mentioned, among others, acetone, cyclohexanone, formaldehyde, benzaldehyde, dimethoxymethane, 2,2-dimethoxypropane, 2-methoxypropene, 1,1-dimethoxycyclohexane, and the like. Among these, acetone, 2-methoxypropene and 2,2-dimethoxypropane are preferred. More preferred is 2,2-dimethoxypropane.

In step (II) of route A according to the invention, the acetal forming reagent is used preferably in an amount of 1 to 10 molar equivalents, more preferably 1 to 5 molar equivalents, relative to the 6-cyano-3,5-dihydroxyhexanoic acid derivative (2). For quickly promoting the reaction, the acetal forming reagent may be used also as a reaction solvent.

As the acid catalyst in step (II) of route A according to the invention, a Lewis acid or a Brønsted acid can be mentioned. As the Lewis acid or Brønsted acid, there may be mentioned, among others, Lewis acids such as aluminum trichloride, boron trifluoride, zinc dichloride and tin tetrachloride; carboxylic acids such as oxalic acid, formic acid, acetic acid, benzoic acid and trifluoroacetic acid; sulfonic acids such as methanesulfonic acid, p-toluenesulfonic acid, camphorsulfonic acid and pyridinium p-toluenesulfonate; and inorganic acids such as hydrochloric acid, sulfuric acid, nitric acid and boric acid. Preferred are p-toluenesulfonic acid, camphorsulfonic acid and pyridinium p-toluenesulfonate.

In step (II) of route A according to the invention, the acid catalyst is used preferably in an amount of 0.001 to 0.5 molar equivalent, more preferably 0.005 to 0.2 molar equivalent, relative to the 6-cyano-3,5-dihydroxyhexanoic acid derivative (2).

In step (II) of route A according to the invention, the reaction may be carried out without using any solvent or in the presence, as a reaction solvent, of any of various organic solvents. As the organic solvents, there may be mentioned, among others, hydrocarbon type solvents such as benzene, toluene and cyclohexane; ether type solvents such as diethyl ether, tetrahydrofuran, 1,4-dioxane, methyl tert-butyl ether and dimethoxyethane; ester type solvents such as ethyl acetate and butyl acetate; ketone type solvents such as acetone and methyl ethyl ketone; halogenated solvents such as methylene chloride, chloroform and 1,1,1-trichloroethane; nitrogen-containing solvents such as dimethylformamide, acetamide, formamide and acetonitrile; and aprotic polar solvents such as dimethyl sulfoxide, N-methylpyrrolidone and hexamethylphosphoric triamide. The above organic solvents may be used singly or two or more of them may be used in combination. Preferred are toluene, acetone, methylene chloride, tetrahydrofuran, dimethylformamide, acetamide, formamide, acetonitrile, dimethyl sulfoxide and N-methylpyrrolidone.

In step (II) of route A according to the invention, the reaction temperature is within the range of −20° C. to 100° C., preferably 0° C. to 50° C.

The reaction time in step (II) of route A according to the invention may vary according to the reaction conditions but is within the range of several minutes to 10 hours.

For recovering the product from the reaction mixture, a conventional procedure for posttreatment may be carried out. Thus, for example, water is added to the reaction mixture after completion of the reaction and an extraction procedure is carried out using a conventional extraction solvent such as ethyl acetate, diethyl ether, methylene chloride, toluene and hexane. The reaction solvent and extraction solvent are distilled off from the thus-obtained extract by a procedure such as heating under reduced pressure, whereupon the desired product is obtained. Such an extraction procedure may be carried out after distilling off the reaction solvent by a procedure such as heating under reduced pressure immediately following completion of the reaction. While the thus-obtained desired product is nearly pure, the purity may further be increased by purification using conventional means such as purification by crystallization, fractional distillation, column chromatography, etc.

Referring to the 6-cyanomethyl-1,3-dioxane-4-acetic acid derivative of the general formula (3):

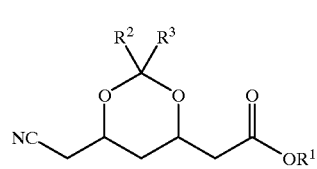

(3)

obtained in step (II) of route A according to the invention, $R^2$ and $R^3$ each independently is a hydrogen atom, an alkyl group containing 1 to 12 carbon atoms, an aryl group containing 6 to 10 carbon atoms or an aralkyl group containing 7 to 12 carbon atoms. As the above alkyl group containing 1 to 12 carbon atoms, aryl group containing 6 to 10 carbon atoms or aralkyl group containing 7 to 12 carbon atoms, there may be mentioned, among others, methyl, ethyl, 1,1-dimethylethyl, hexyl, dodecanyl, phenyl, tolyl, naphthyl, benzyl, p-methoxybenzyl, naphthylethyl and the like. Preferred is methyl.

The 6-cyanomethyl-1,3-dioxane-4-acetic acid derivative (3) retains the configuration of each of the two asymmetric carbon atoms of the 6-cyano-3,5-dihydroxyhexanoic acid derivative (2) used and, thus, the (3S, 5R)-, (3S, 5S)-, (3R, 5R)- and (3R, 5S)-6-cyano-3,5-dihydroxyhexanoic acid derivatives give the corresponding (4S, 6R)-, (4S, 6S)-, (4R, 6R)- and (4R, 6S)-6-caynomethyl-1,3-dioxane-4-acetic acid derivatives, respectively. The (4R, 6R) isomer of the following general formula (6):

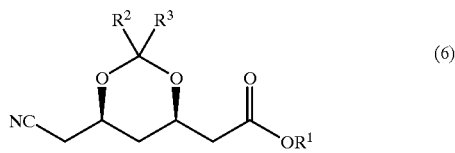

is preferred.

Therefore, the most preferred 6-cyanomethyl-1,3-dioxane-4-acetic acid derivative (3), namely 1,1-dimethylethyl (4R,6R)-6-cyanomethyl-2,2-dimethyl-1,3-dioxane-4-acetate, can be produced from the most preferred 6-cyano-3,5-dihydroxyhexanoic acid derivative (2), namely 1,1-dimethylethyl (3R, 5R)-6-cyano-3,5-dihydroxyhexanoate.

In step (III) of route B according to the invention, on the other hand, the acetal forming reagent includes, among others, a ketone, an aldehyde, an alkoxyalkane, an alkoxyalkene and so on. As specific examples of the above ketone, aldehyde, alkoxyalkane and alkoxyalkene, there may be mentioned, among others, acetone, cyclohexanone, formaldehyde, benzaldehyde, dimethoxymethane, 2,2-dimethoxypropane, 2-methoxypropene, 1,1-dimethoxycyclohexane, and the like. Among these, acetone, 2-methoxypropene and 2,2-dimethoxypropane are preferred. More preferred is 2,2-dimethoxypropane.

In step (III) of route B according to the invention, the acetal forming reagent is used preferably in an amount of 1 to 10 molar equivalents, more preferably 1 to 5 molar equivalents, relative to the 3,5-dihydroxy-6-halohexanoic acid derivative (1). For quickly promoting the reaction, the acetal forming reagent may be used as a reaction solvent.

In step (III) of route B according to the invention, a Lewis acid or a Brønsted acid may be used as the acid catalyst. As the Lewis acid or Brønsted acid, there may be mentioned, among others, Lewis acids such as aluminum trichloride, boron trifluoride, zinc dichloride and tin tetrachloride; carboxylic acids such as oxalic acid, formic acid, acetic acid, benzoic acid and trifluoroacetic acid; sulfonic acids such as methanesulfonic acid, p-toluenesulfonic acid, camphorsulfonic acid and pyridinium p-toluenesulfonate; and inorganic acids such as hydrochloric acid, sulfuric acid, nitric acid and boric acid. Preferred are p-toluenesulfonic acid, camphorsulfonic acid and pyridinium p-toluenesulfonate.

In step (III) of route B according to the invention, the acid catalyst is used preferably in an amount of 0.001 to 0.5 molar equivalent, more preferably 0.005 to 0.2 molar equivalent, relative to the 3,5-dihydroxy-6-halohexanoic acid derivative (1).

In step (III) of route B according to the invention, the reaction may be carried out without using any solvent or in the presence, as a reaction solvent, of any of various organic solvents. As the organic solvents, there may be mentioned, among others, hydrocarbon type solvents such as benzene, toluene and cyclohexane; ether type solvents such as diethyl ether, tetrahydrofuran, 1,4-dioxane, methyl tert-butyl ether and dimethoxyethane; ester type solvents such as ethyl acetate and butyl acetate; ketone type solvents such as acetone and methyl ethyl ketone; halogenated solvents such as methylene chloride, chloroform and 1,1,1-trichloroethane; nitrogen-containing solvents such as dimethylformamide, acetamide, formamide and acetonitrile; and aprotic polar solvents such as dimethyl sulfoxide, N-methylpyrrolidone and hexamethylphosphoric triamide. The above organic solvents may be used singly or two or more of them may be used in combination. Preferred are toluene, acetone, methylene chloride, tetrahydrofuran, dimethylformamide, acetamide, formamide, acetonitrile, dimethyl sulfoxide and N-methylpyrrolidone.

In step (III) of route B according to the invention, the reaction temperature is within the range of –20° C. to 100° C., preferably 0° C. to 50° C.

The reaction time in step (III) of route B according to the invention may vary according to the reaction conditions but is within the range of several minutes to 10 hours.

For recovering the product from the reaction mixture, a conventional procedure for posttreatment may be carried out. Thus, for example, water is added to the reaction mixture after completion of the reaction and an extraction procedure is carried out using a conventional extraction solvent such as ethyl acetate, diethyl ether, methylene chloride, toluene and hexane. The reaction solvent and extraction solvent are distilled off from the thus-obtained extract by a procedure such as heating under reduced pressure, whereupon the desired product is obtained. Such an extraction procedure may be carried out after distilling off the reaction solvent by a procedure such as heating under reduced pressure immediately following completion of the reaction. While the thus-obtained desired product is nearly pure, the purity may further be increased by purification using conventional means such as purification by crystallization, fractional distillation, column chromatography, etc.

Referring to the 6-halomethyl-1,3-dioxane-4-acetic acid derivative of the general formula (7):

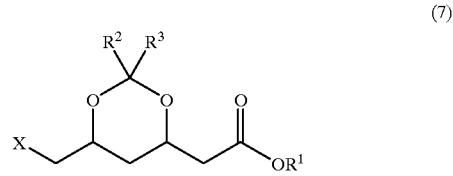

obtained in step (III) of route B according to the invention, $R^2$ and $R^3$ each independently is a hydrogen atom, an alkyl group containing 1 to 12 carbon atoms, an aryl group containing 6 to 10 carbon atoms or an aralkyl group containing 7 to 12 carbon atoms. As the above alkyl group containing 1 to 12 carbon atoms, aryl group containing 6 to 10 carbon atoms or aralkyl group containing 7 to 12 carbon atoms, there may be mentioned, among others, methyl, ethyl, 1,1-dimethylethyl, hexyl, dodecanyl, phenyl, tolyl, naphthyl, benzyl, p-methoxybenzyl, naphthylethyl and the like. Preferred is methyl.

The 6-halomethyl-1,3-dioxane-4-acetic acid derivative (7) retains the configuration of each of the two asymmetric carbon atoms of the 3,5-dihydroxy-6-halohexanoic acid derivative (1) used and, thus, the (3S, 5S)-, (3S, 5R)-, (3R, 5S)- and (3R, 5R)-3,5-dihydroxy-6-halohexanoic acid derivatives give the corresponding (4S, 6S)-, (4S, 6R)-, (4R, 6S)- and (4R, 6R)-6-halomethyl-1,3-dioxane-4-acetic acid derivatives, respectively. The (4R, 6S) isomer of the general formula (8):

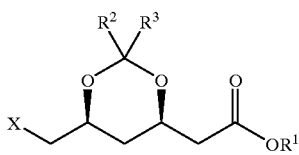

(8)

is preferred.

Therefore, the most preferred 6-halomethyl-1,3-dioxane-4-acetic acid derivative (7), namely 1,1-dimethylethyl (4R, 6S)-6-chloromethyl-2,2-dimethyl-1,3-dioxane-4-acetate, can be produced from the most preferred 3,5-dihydroxy-6-halohexanoic acid derivative (1), namely 1,1-dimethylethyl (3R, 5S)-6-chloro-3,5-dihydroxyhexanoate.

In step (IV) of route B according to the invention, a cyanide can be used as the cyanating agent. The cyanide includes, among others, sodium cyanide, potassium cyanide, calcium cyanide, silver cyanide, tetraethylammonium cyanide, tetrabutylammonium cyanide and the like. Preferred is sodium cyanide or potassium cyanide.

In step (IV) of route B according to the invention, the cyanating agent is used preferably in an amount of 1 to 5 molar equivalents, more preferably 1 to 2 molar equivalents, relative to the 6-halomethyl-1,3-dioxane-4-acetic acid derivative (7).

As the solvent which can be used in step (IV) of route B according to the invention, there may be mentioned, for example, water and an organic solvent. The organic solvent includes, among others, alcohol type solvents such as methanol, ethanol, butanol, isopropyl alcohol, ethylene glycol and methoxyethanol; hydrocarbon type solvents such as benzene, toluene and cyclohexane; ether type solvents such as diethyl ether, tetrahydrofuran, 1,4-dioxane, methyl tert-butyl ether and dimethoxyethane; ester type solvents such as ethyl acetate and butyl acetate; ketone type solvents such as acetone and methyl ethyl ketone; halogenated solvents such as methylene chloride, chloroform and 1,1,1-trichloroethane; nitrogen-containing solvents such as dimethylformamide, acetamide, formamide and acetonitrile; aprotic polar solvents such as dimethyl sulfoxide, N-methylpyrrolidone and hexamethylphosphoric triamide; and so forth. The above solvents may be used singly or two or more of them may be used in combination. Preferred are water, dimethylformamide, acetamide, formamide, acetonitrile, dimethyl sulfoxide, N-methylpyrrolidone and the like.

In step (IV) of route B according to the invention, the reaction temperature is within the range of 0° C. to 150° C., preferably 20° C. to 100° C.

The reaction time in step (IV) of route B according to the invention may vary depending on the reaction conditions but is generally several minutes to 10 hours.

For recovering the product from the reaction mixture, a conventional procedure for posttreatment may be carried out. Thus, for example, water is added to the reaction mixture after completion of the reaction, and an extraction procedure is carried out using a conventional extraction solvent such as ethyl acetate, diethyl ether, methylene chloride, toluene, hexane or the like. The reaction solvent and extraction solvent are distilled off from the thus-obtained extract by a procedure such as heating under reduced pressure, whereupon the desired product is obtained. Such an extraction procedure may be carried out after distilling off the reaction solvent by a procedure such as heating under reduced pressure immediately following completion of the reaction. While the thus-obtained product is nearly pure, the purity may further be increased by purification using conventional means such as purification by crystallization, fractional distillation, column chromatography, etc.

The 6-cyanomethyl-1,3-dioxane-4-acetic acid derivative of the general formula (3):

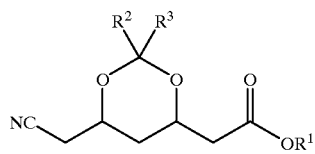

(3)

obtained in step (IV) of route B according to the invention retains the configuration of each of the two asymmetric carbon atoms of the 6-halomethyl-1,3-dioxane-4-acetic acid derivative (7) used and, thus, the (4S, 6S)-, (4S, 6R)-, (4R, 6S)- and (4R, 6R)-6-halomethyl-1,3-dioxane-4-acetic acid derivatives give the corresponding (4S, 6R)-, (4S, 6S)-, (4R, 6R)- and (4R, 6S)-6-caynomethyl-1,3-dioxane-4-acetic acid derivatives, respectively. Preferred is the (4R, 6R) isomer of the same general formula (6) as given above.

Therefore, the most preferred 6-cyanomethyl-1,3-dioxane-4-acetic acid derivative (3), namely 1,1-dimethylethyl (4R, 6R)-6-cyanomethyl-2,2-dimethyl-1,3-dioxane-4-acetate, can be produced from the most preferred 6-halomethyl-1,3-dioxane-4-acetic acid derivative (7), namely 1,1-dimethylethyl (4R, 6S)-6-chloromethyl-2,2-dimethyl-1,3-dioxane-4-acetate.

BEST MODES FOR CARRYING OUT THE INVENTION

The following examples illustrate the present invention in further detail. These examples are, however, by no means limitative of the scope of the present invention.

The $^1$H nuclear magnetic resonance spectra ($^1$H NMR) and $^{13}$C nuclear magnetic resonance spectra ($^{13}$C NMR) given in the following examples were measured on a Nippon Denshi model EX-400.

EXAMPLE 1

Synthesis of 1,1-dimethylethyl (3R, 5R)-6-cyano-3,5-dihydroxyhexanoate 1,1-Dimethylethyl (3R, 5S)-6-chloro-3,5-dihydroxyhexanoate (synthesized by the method described in the specification of U.S. Pat. No. 5,278,313) (238 mg, 1.0 mmol) was dissolved in 2.0 ml of dimethylformamide, and 0.5 ml of aqueous solution of sodium cyanide (50 mg, 1.0 mmol) was added dropwise. After 2 hours of stirring at 80° C., the reaction mixture was cooled to room temperature, 10 ml of water added thereto, and the whole mixture was extracted five times with ethyl acetate.

The extract organic layer was washed with a saturated aqueous solution of sodium chloride and then dried over anhydrous sodium sulfate, and the solvents were distilled off under reduced pressure. The thus-obtained oil was purified by silica gel column chromatography (Merck's Kieselgel 60; hexane:ethyl acetate=50:50) to give 185 mg (yield 81%) of 1,1-dimethylethyl (3R, 5R)-6-cyano-3,5-dihydroxyhexanoate as an oil.

$^1$H-NMR (CDCl$_3$, 400 MHz/ppm); 1.47 (9H, s), 1.72 (2H, dd), 2.43 (2H, dd), 2.55 (2H, dd), 3.96 (1H, bd), 4.21 (1H, bt), 4.23–4.34 (1H, m), 4.25 (1H, bs); $^{13}$C-NMR (CDCl$_3$, 100MHz/ppm); 25.8, 28.1, 40.8, 41.9, 67.9, 68.7, 82.1, 117.4, 172.1.

EXAMPLE 2

Synthesis of 1,1-dimethylethyl (4R, 6R)-6-cyanomethyl-2,2-dimethyl-1,3-dioxane-4-acetate 1,1-Dimethylethyl (3R, 5R)-6-cyano-3,5-dihydroxyhexanoate (229 mg, 1.0 mmol) was dissolved in 1.0 ml of acetone, 0.49 ml (4.0 mmol) of 2,2-dimethoxypropane and 5.2 mg (0.05 mmol) of pyridinium p-toluenesulfonate were added in that order, and the mixture was stirred at room temperature for 5 hours. The reaction solvent and excess 2,2-dimethoxypropane were distilled off under reduced pressure, 10 ml of water was added to the residue, and the mixture was extracted three times with ethyl acetate.

The extract organic layer was washed with a saturated aqueous solution of sodium chloride and then dried over anhydrous sodium sulfate, and the solvent was distilled off under reduced pressure. The thus-obtained oil was purified by silica gel column chromatography (Merck's Kieselgel 60; hexane:ethyl acetate=80:20) to give 229 mg (yield 85%) of 1,1-dimethylethyl (4R, 6R)-6-cyanomethyl-2,2-dimethyl-1,3-dioxane-4-acetate as a white solid.

$^1$H-NMR (CDCl$_3$, 400 MHz/ppm); 1.32 (1H, dd), 1.39 (3H, s), 1.45 (9H, s), 1.46 (3H, s), 1.75 (1H, dt), 2.34 (1H, dd), 2.46 (1H, dd), 2.51 (2H, t), 4.12–4.17 (1H, m), 4.26–4.31 (1 $^{13}$C-NMR (CDCl$_3$, 100MHz/ppm); 19.6, 25.0, 28.1, 29.7, 35.4, 42.3, 65.1, 65.7, 80.9, 99.5, 116.8, 169.9.

EXAMPLE 3

Synthesis of 1,1-dimethylethyl (4R, 6S)-6-chloromethyl-2,2-dimethyl-1,3-dioxane-4-acetate 1,1-Dimethylethyl (3R, 5S)-6-chloro-3,5-dihydroxyhexanoate (synthesized by the method described in the specification of U.S. Pat. No. 5,278,313) (476 mg, 2.0 mmol) was dissolved in 2.0 ml of acetone, 0.49 ml (4.0 mmol) of 2,2-dimethoxypropane and 10.4 mg (0.10 mmol) of pyridinium p-toluenesulfonate were added in that order, and the mixture was stirred at room temperature for 6 hours. The reaction solvent and excess 2, 2-dimethoxypropane were then distilled off under reduced pressure, 10 ml of water was added to the residue, and the mixture was extracted three times with ethyl acetate.

The extract organic layer was washed with a saturated aqueous solution of sodium chloride and then dried over anhydrous sodium sulfate, and the solvent was distilled off under reduced pressure to give 510 mg (yield 92%) of 1,1-dimethylethyl (4R, 6S)-6-chloromethyl-2,2-dimethyl-1, 3-dioxane-4-acetate.

$^1$H-NMR (CDCl$_3$, 400 MHz/ppm); 1.25 (1H, dd), 1.39 (3H, s), 1.45 (9H, s), 1.47 (3H, s), 1.77 (1H, dt), 2.33 (1H, dd), 2.46 (1H, dd), 2.40 (1H, dd), 2.51 (1H, dd), 4.03–4.10 (1H, m), 4.25–4.30 (1H, m); $^{13}$C-NMR (CDCl$_3$, 100 MHz/ppm); 19.7, 28.1, 29.8, 34.0, 42.6, 47.1, 65.9, 69.2, 80.8, 99.3, 170.1.

EXAMPLE 4

Synthesis of 1,1-dimethylethyl (4R, 6R)-6-cyanomethyl-2,2-dimethyl-1,3-dioxane-4-acetate 1,1-Dimethylethyl (4R, 6S)-6-chloromethyl-2,2-dimethyl-1,3-dioxane-4-acetate (278.1 mg, 1.0 mmol) was dissolved in 2.0 ml of dimethyl sulfoxide, and 0.5 ml of aqueous solution of sodium cyanide (100 mg, 2.0 mmol) was added dropwise. After 30 hours of stirring at 100° C., the reaction mixture was cooled to room temperature, 10 ml of water was added thereto, and the mixture was extracted three times with n-hexane. The extract organic layer was washed with a saturated aqueous solution of sodium chloride and then dried over anhydrous sodium sulfate, and the solvents were distilled off under reduced pressure.

The thus-obtained oil was purified by silica gel column chromatography (Merck's Kieselgel 60; hexane:ethyl acetate=80:20) to give 28 mg (yield 11%) of 1,1-dimethylethyl (4R, 6R)-6-cyanomethyl-2,2-dimethyl-1,3-dioxane-4-acetate as a white solid.

INDUSTRIAL APPLICABILITY

The present invention, which has the above constitution, can produce intermediates of medicinal compounds, in particular 6-cyanomethyl-1,3-dioxane-4-acetic acid derivatives, which are important intermediates for the production of the HMG coenzyme A reductase inhibitor atrovastatin, and optically active forms thereof from raw materials readily available on the market at low cost and in high yields.

What is claimed is:

1. A process for producing a 6-cyanomethyl-1,3-dioxane-4-acetic acid derivative of the general formula (3):

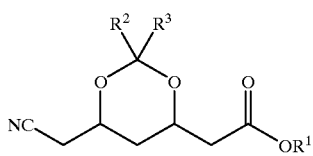

(3)

wherein $R^1$, $R^2$ and $R^3$ each independently represents a hydrogen atom, an alkyl group containing 1 to 12 carbon atoms, an aryl group containing 6 to 10 carbon atoms or an aralkyl group containing 7 to 12 carbon atoms, which comprises reacting the 3,5-dihydroxy-6-halohexanoic acid derivative of the general formula (1):

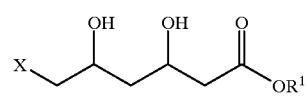

(1)

wherein $R^1$ is as defined above and X represents a halogen atom, with a cyanating agent to provide a 6-cyano-3,5-dihydroxyhexanoic acid derivative of the general formula (2):

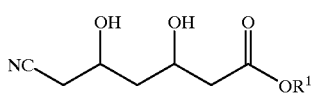

(2)

wherein $R^1$ is as defined above,
followed by an acetal formation reaction of the same with an acetal forming reagent in the presence of an acid catalyst.

2. The process according to claim 1,
wherein a (3R, 5S)-3,5-dihydroxy-6-halohexanoic acid derivative of the general formula (4):

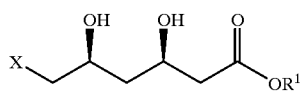

(4)

wherein
R[1] represents a hydrogen atom, an alkyl group containing 1 to 12 carbon atoms, an aryl group containing 6 to 10 carbon atoms or an aralkyl group containing 7 to 12 carbon atoms, and X represents a halogen atom, is used as the compound of the general formula (1), and this is subjected to a reaction with a cyanating agent to provide a (3R, 5R)-6-cyano-3,5-dihydroxyhexanoic acid derivative of the general formula (5):

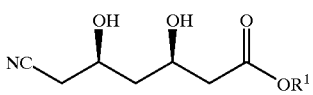

(5)

wherein R[1] is as defined above,
followed by an acetal formation reaction of the same with an acetal forming reagent in the presence of an acid catalyst to give a (4R, 6R)-6-cyanomethyl-1,3-dioxane-4-acetic acid derivative of the general formula (6):

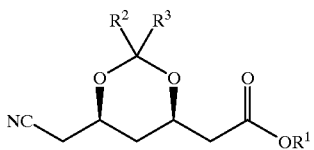

(6)

wherein R[1] is as defined above, and R[2] and R[3] each independently represents a hydrogen atom, an alkyl group containing 1 to 12 carbon atoms, an aryl group containing 6 to 10 carbon atoms or an aralkyl group containing 7 to 12 carbon atoms.

3. The process according to claim 1, wherein X is a chlorine atom.

4. The process according to claim 1, wherein R[1] is a 1,1-dimethylethyl group.

5. The process according to claim 1, wherein the cyanating agent is sodium cyanide or potassium cyanide.

6. The process according to claim 1, wherein R[2] and R[3] each is a methyl group.

7. The process according to claim 1, wherein the acid catalyst is p-toluenesulfonic acid, camphosulfonic acid or pyridinium p-toluenesulfonate.

8. The process according to claim 6, wherein 2,2-dimethoxypropane is used as the acetal forming reagent.

9. The process according to claim 2, wherein R[2] and R[3] each is a methyl group.

10. The process according to claim 2, wherein the acid catalyst is p-toluenesulfonic acid, camphosulfonic acid or pyridinium p-toluenesulfonate.

11. A process for producing a 6-cyano-3,5-dihydroxyhexanoic acid derivative of the general formula (2):

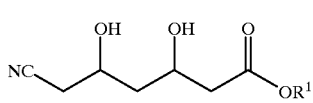

(2)

wherein R[1] represents a hydrogen atom, an alkyl group containing 1 to 12 carbon atoms, an aryl group containing 6 to 10 carbon atoms or an aralkyl group containing 7 to 12 carbon atoms, which comprises reacting, with a cyanating agent, a 3,5-dihydroxy-6-halohexanoic acid derivative of the general formula (1):

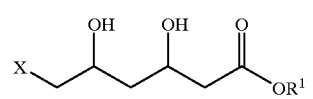

(1)

wherein R[1] is as defined above, and X represents a halogen atom.

12. The process according to claim 11,
wherein a (3R, 5S)-3,5-dihydroxy-6-halohexanoic acid derivative of the general formula (4):

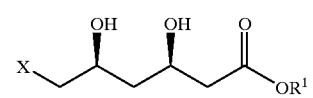

(4)

wherein
R[1] represents a hydrogen atom, an alkyl group containing 1 to 12 carbon atoms, an aryl group containing 6 to 10 carbon atoms or an aralkyl group containing 7 to 12 carbon atoms, and X represents a halogen atom, is used as the compound of the general formula (1) and the same is reacted with a cyanating agent to give a (3R, 5R)-6-cyano-3,5-dihydroxyhexanoic acid derivative of the general formula (5):

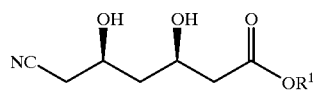

(5)

wherein R[1] is as defined above.

* * * * *